(12) United States Patent
Levin (10) Patent No.: US 7,137,978 B2
(45) Date of Patent: Nov. 21, 2006

(54) CRYOSURGICAL INSTRUMENT AND ITS ACCESSORY SYSTEM

(75) Inventor: Alexander Levin, Binyamina (IL)

(73) Assignee: Arbel Medical Ltd, Yokneam (IL)

( * ) Notice: Subject to any disclaimer, the term of this patent is extended or adjusted under 35 U.S.C. 154(b) by 113 days.

(21) Appl. No.: 10/637,904

(22) Filed: Aug. 11, 2003

(65) Prior Publication Data

US 2004/0078033 A1    Apr. 22, 2004

(30) Foreign Application Priority Data

Aug. 26, 2002   (IL) ..................................... 151486

(51) Int. Cl.
*A61B 18/18*   (2006.01)

(52) U.S. Cl. .......................................... 606/22; 606/21

(58) Field of Classification Search ............. 606/20–26
See application file for complete search history.

(56) References Cited

U.S. PATENT DOCUMENTS

| | | | | |
|---|---|---|---|---|
| 3,971,383 A | * | 7/1976 | van Gerven | 606/23 |
| 5,254,116 A | * | 10/1993 | Baust et al. | 606/23 |
| 5,573,532 A | * | 11/1996 | Chang et al. | 606/26 |
| 5,674,218 A | * | 10/1997 | Rubinsky et al. | 606/20 |
| 5,716,353 A | * | 2/1998 | Matsuura et al. | 606/22 |
| 6,251,105 B1 | * | 6/2001 | Mikus et al. | 606/22 |
| 6,468,268 B1 | * | 10/2002 | Abboud et al. | 606/20 |
| 6,551,309 B1 | * | 4/2003 | LePivert | 606/20 |

\* cited by examiner

Primary Examiner—Michael Peffley
(74) Attorney, Agent, or Firm—Sean Kelleher; Bruce Lilling (57) ABSTRACT

The invention is directed to a cryosurgical instrument and to an accessory system operating on the base of refrigerant evaporation, wherein the portions of the refrigerant are periodically provided to the distal cryotip of the cryosurgical instrument via a central lumen thereof. The internal surface of the distal cryotip is preferably covered by a porous coating capable of soaking at least one portion of the refrigerant. The vapors obtained as a result of the refrigerant boiling on the porous coating of the cryotip are preferably removed through the central lumen of the cryosurgical instrument into the atmosphere. These features may be combined to construct a cryosurgical instrument with relatively high freezing power and small outer diameter which may be designed as a flexible cryocatheter or alternatively as a rigid cryoprobe.

22 Claims, 7 Drawing Sheets

CRYOSURGICAL INSTRUMENT AND ITS ACCESSORY SYSTEM

CROSS REFERENCE APPLICATION

This patent application claims the benefit of the earlier filed Israeli Patent Application Ser. No. 151486 Filed Aug. 26, 2002.

FEDERALLY SPONSORED RESEARCH OR DEVELOPMENT

Not Applicable.

BACKGROUND OF THE INVENTION

There is a significant number of patents which describe different constructions of cryosurgical probes and catheters. These patents aims to solve some of the problems, which are common to the cryosurgical probes and catheters of the prior art.

One of these problems is the construction of relatively cheap and simple probes or catheters with high reliability and sufficiently effective thermal insulation of their lateral non-operating walls. Moreover, cryosurgical catheters should have high flexibility, especially, when they are used for cardiac procedures. In addition, the closed distal end (cryotip) of such probe or catheter must provide in many cases high specific freezing capacity at sufficiently low-temperatures.

Analysis of United States patents related to this field shows, that the structure of the proposed probes and catheters intended for cryosurgery does not satisfy the above-mentioned requirements.

For example, U.S. Pat. No. 3,971,383 proposes a cryogenic surgical instrument with a coaxial assembly of flexible tubes, wherein the inner tube is connected to a supply of cryogenic liquid, and the space between the outer wall of the inner tube and the inner wall of an intermediate tube forms a return line for evaporated cryogenic liquid, which is vented to the atmosphere. The space between the outermost coaxial tube and the intermediate tube contains a gas, such as normal butane, for providing thermal insulation of the inner and intermediate lumens.

U.S. Pat. No. 5,716,353 describes a probe for cryosurgery which consists of three tubes: an inner tube for supplying a cryogenic refrigerant to a cryotip positioned at the distal end of an outer jacket tube, and an intermediate tube situated concentrically around the inner tube. The channel between the inner and intermediate tubes serves as venting path for venting cryogenic refrigerant from the freezing zone. This construction is simple, but it does not provide sufficient thermal insulation as required in the construction of cryogenic catheters. Consequently, it may cause over-heating of the vented cryogenic refrigerant, as well as over-cooling of tissues adjacent to the intermediate section of the catheter.

U.S. Pat. No. 5,573,532 describes a cryosurgical instrument which comprises tubes for cryogenic fluid supply and for the return of cryogenic fluid vapors, wherein these tubes are concentric and the return tube is sealed with a cryotip. Vacuum insulation of the return lumen is also proposed. However, this construction is relatively expensive and has low reliability. In addiiton, the proposed vacuum insulation limits the flexibility of the probe, especially, when it is very long, as in the case of catheter implementations.

U.S. Pat. No. 5,674,218 describes a cryosurgical instrument, a system and method of cryosurgery. According to this patent a cryogenic liquid (preferably, liquid nitrogen) is initially sub-cooled below its normal boiling point and in that state supplied into the open proximal end of the internal supply line. The outer lumen of the cryosurgical instrument is provided with active vacuum insulation.

Obviously, this construction cannot provide high flexibility and therefore cannot be used as the basis for construction of a catheter for use in cryosurgery.

U.S. Pat. No. 5,254,116 describes a cryocatheter with a set of vent holes in the lateral wall of a central feeding lumen, wherein sub-cooled liquid nitrogen is delivered into the central feeding lumen as a cryogenic liquid. This construction, however does not ensure proper thermal insulation of the cryocatheter.

BRIEF SUMMARY OF THE INVENTION

This invention proposes novel designs for a cryosurgical instrument and for its accessory system. The cryosurgical instrument of the present invention is constructed from two major sub-units:

i) a distal cryotip, which is used to contact the target tissue to be treated, wherein the freezing of the cryotip is obtained by evaporation of a cryogenic liquid on its internal surface, said internal surface being covered with a porous coating having open porosity; and ii) an elongated tubular sub-unit for delivering portions of the cryogenic liquid to the distal cryotip and for removing vapors generated in the process of the boiling of the cryogenic liquid in the porous coating of the distal cryotip.

The elongated tubular sub-unit comprises an external shaft comprising a central feeding-venting tube, the lumen of which is used to supply portions of the cryogenic liquid to the porous coating of the distal cryotip and, at the same time, to remove the vapors generated in the process of boiling the cryogenic liquid on the internal surface of the distal cryotip into the atmosphere or into a vacuum pump.

In addition, a coaxial tubular piece is positioned in the space between the distal sections of the central feeding-venting lumen and the external shaft, the distal end of said tubular piece being sealed by the external shaft or by the cryotip itself, and its proximal end being sealed by the central feeding-venting tube. Said coaxial tubular piece forms a buffer space between the internal surface of the cryotip's shaft and the outer surface of the central feeding-venting tube, such that said buffer space facilitates flow of the portion the cryogenic liquid in the central feeding-venting tube toward the cryotip.

The proximal section of the external shaft and the proximal end of the central feeding-venting tube are provided with inlet-outlet connections.

According to another embodiment of the invention a coaxial intermediate lumen situated between the central feeding-venting lumen and the external shaft replaces the aforementioned coaxial tubular piece, wherein the distal end of this coaxial intermediate lumen is sealed by the external shaft or by the cryotip itself and its proximal end is sealed by the central feeding-venting tube. The proximal end of the external shaft is sealed by the wall of the proximal section of the coaxial intermediate lumen. The proximal section of the coaxial intermediate lumen is provided in this case with an outlet connection.

When this proposed device is used as a cryocatheter, the external shaft is made from a polymer material that provides high flexibility.

The cryotip of the cryocatheter is made from material with high thermal conductivity (for example, copper, silver, diamond, BeO), and its internal surface is advantageously covered with a porous coating having open porosity (for example, the porous coating that is obtained by sintering copper powder). These features permit high heat transfer coefficients values in the process of boiling the cryogenic liquid. Additionally, the porous coating is adapted to soak completely one portion of the cryogenic liquid provided by an accessory system during the first quarter-period (the first operating state in one operating cycle) of its operation, as will be described hereinafter.

The cryocatheter of the invention can be used for inhibiting restenosis of a blood vessel. In this case the cryotip is constructed in a tubular shape, the distal end of the tubular shaped cryotip is sealed with a plug made from a polymer with low thermal conductivity, and its tubular section is fabricated from a thin polymer film of high elasticity. The internal surface of the tubular section is coated with a porous polymer layer having open porosity and high elasticity.

The construction of preferable accessory systems for the cryocatheter (or cryoprobe) of the invention will be now described in detail.

A first embodiment of the accessory system, which achieves the functioning required for the proposed cryosurgical instrument, comprises: a thermo-insulated tank filled with the cryogenic liquid, wherein the thermo-insulated tank is provided with a relief valve which enables to preset the desired pressure in the thermo-insulated tank; a feed pipe which is situated vertically such that its lower end is positioned in the thermo-insulated tank and near its bottom. An outlet connection of the feed pipe is joined by a flexible thermo-insulated duct with an inlet connection of a multi-way valve. This multi-way valve comprises one additional inlet connection which communicates with a bottle containing pressurized gas (for example, nitrogen), and two outlets communicating with the atmosphere (or a vacuum pump) and with an inlet-outlet connection that communicates with an inlet-outlet connection of the central feeding-venting tube of the cryosurgical instrument.

The accessory system comprises four shut-off valves, the first of which is installed on a main duct that communicates between the multi-way valve and the inlet-outlet connection of the central feeding-venting tube of the cryosurgical instrument, the second—on a duct that communicates between the outlet connection of the thermo-insulated tank and the multi-way valve, the third—on the duct that communicates between the bottle comprising the pressurized gas and the multi-way valve, and the fourth—on the thermo-insulated tank; where this fourth shut-off valve is used for filling the thermo-insulted tank with the cryogenic liquid. The fourth shut-off valve is normally opened while filling the thermo-insulated tank with the cryogenic liquid. The second shut-off valve is used for cutting off the supply of the cryogenic liquid to the multi-way valve. The third shut-off valve is used for cutting off the supply of pressurized gas to the multi-way valve and the first shut-off valve for operating the cryosurgical instrument.

An electromechanical (or pneumatic) drive is used to perform a periodical changeover of the multi-way valve state at a preset changeover frequency for periodically communicating between the inlet-outlet connection of the central feeding-venting tube and the thermo-insulated tank, the bottle comprising the pressurized gas, and the atmosphere (or the vacuum pump).

A control unit used for controlling the changeover frequency of the multi-way valve, or for halting its operation in case of significant deviations from the preset frequency. The control unit also activates the aforementioned second and third shut-off valves. In addition, it is also possible to install pressure and temperature gauges on the main duct of the central feeding-venting tube of the accessory system. Data obtained from these gauges is processed by the control unit and in cases of significant deviations of the measured parameters from the preset values, the control unit cuts off the shut-off valves.

Portions of the cryogenic liquid, which remain in the porous coating of the cryotip and in the aforementioned buffer space in the period between communicating between the central feeding-venting tube and the inlet connection of the vacuum pump (or with the atmosphere) and with the feeding pipe of the thermo-insulated tank, generate reasonably high pressure in the central feeding-venting tube which may cause difficulties in introducing another portion of the cryogenic liquid into the central feeding-venting tube.

In the aforementioned embodiment, which utilizes a coaxial intermediate lumen with an outlet connection instead of the coaxial tubular piece, there is an auxiliary shut-off valve installed on a duct communicating between the outlet connection of the coaxial intermediate lumen and the atmosphere (or with the vacuum pump), wherein this shut-off valve is mechanically or electro-mechanically coupled to the multi-way valve such that it is opened only at a quarter-period, when the multi-way valve is communicating between the main duct and the bottle comprising the pressurized gas.

In addition, the outlet connection of the intermediate lumen can serve as an inlet-outlet connection. In this case, a gas contained in a special bottle is provided into the gap between the coaxial intermediate lumen and the central feeding-venting tube whenever the multi-way valve communicates between the central feeding-venting lumen and the atmosphere (or the vacuum pump).

The ducts connecting between the thermo-insulated tank and the multi-way valve, and between the multi-way valve and the inlet-outlet connection of the central feeding-venting tube can be provided with an outer thermal insulation, for example, vacuum insulation.

There are various cryogens that can be used as cryogenic liquids, such as liquid nitrogen, liquid argon, liquid R14 and others.

In addition, it is possible to utilize two tanks with different cryogenic liquids. For example, the first tank may comprise a cryogenic liquid having low boiling temperature (for example, liquid nitrogen), which is used for cryogenic treatment of a target tissue, and the second tank may comprise a cryogenic liquid having a relatively high boiling temperature (for example, R12B1 that boils at a temperature −3.8° C. at atmospheric pressure), where this second liquid is used for ice-mapping.

The second liquid having a normal boiling temperature higher than 0° C. (for example, R11, which has normal boiling temperature 23.65° C.) can be used for fast thawing a tissue, which has been previously frozen by the cryogenic liquid.

Application of two liquids with a large difference in their boiling temperatures requires performance of blowing out the central feeding-venting tube, the buffer space, and several ducts, in the period between the procedures of ice-mapping and cryogenic treatment which may follow it.

The accessory system comprises in this case two accessory sub-systems, each of which is constructed substantially similar to the accessory system which has been described hereinabove. The accessory sub-systems have a common control unit and a common main duct which splits off into two ducts each communicating with a first and a second multi-way valves. A thermo-insulated tank of the first accessory sub-system contains a cryogenic liquid that is used for freezing the target tissue, and the thermo-insulated tank of the second accessory subunit contains a liquid with relatively high boiling temperature (for example, R12B1) which is used for preliminary ice-mapping.

The accessory system also comprises an auxiliary accessory sub-system, which is used for blowing out the cryosurgical instrument and the ducts communicating the first and second accessory sub-systems with the cryosurgical instrument. The auxiliary accessory sub-system consists of an auxiliary bottle with pressurized gas and an auxiliary three-way valve, which is installed on a duct communicating the auxiliary bottle with the main duct. The auxiliary three-way valve is regulated by the common control unit, and it has two outlet connections; the first of which communicates with the main duct and the second with the atmosphere or with a vacuum pump.

The blowing out process is performed by closing the shut-off valves that are installed on the ducts communicating between the thermo-insulated tanks and their respective multi-way valves followed by blowing the pressurized gas from the auxiliary bottle into the main duct and the ducts splitting therefrom, and into the central feeding-venting tube and the buffer space by a charging and purging technique.

As was previously discussed hereinabove, the gap between the central feeding-venting tube (or the coaxial tubular piece) and the external shaft that is used for thermally insulating the external shaft, especially, its distal section, in order to prevent the possibility of a negative temperature on its outer surface.

It is of course possible to achieve a higher degree of thermal insulation of the external shaft of the cryosurgical instrument by first of all filling the gap between the external shaft and the coaxial tubular piece with a gas which has, on the one hand, very low thermal conductivity and, on the other hand, a condensation temperature that is lower than the boiling temperature of the cryogenic liquid. For this purpose, the proximal section of the external shaft is provided with an inlet-outlet connection and the accessory system is provided with an additional bottle comprising the aforementioned gas having low thermal conductivity, and with a duct that communicates between the additional bottle and the inlet-outlet connection of the external shaft, wherein said duct is provided with a three-way valve which communicates with the atmosphere or with a vacuum pump. This sub-system allows filling of the gap between the external shaft and the coaxial tubular piece by means of a charging and purging technique.

In order to achieve better thermal insulation properties of the distal section of the external shaft (i.e. to prevent its outer surface having a negative temperature) it is possible to apply the heat pipe principle.

In this case, the heat pipe principle is realized in the following manner: the outer surfaces of the coaxial tubular piece and a section of the central feeding-venting tube matching this coaxial tubular piece are covered with a porous coating with open porosity, the purpose of this coating being to function as a wick. The gap between the external shaft and the coaxial tubular piece, and its extension to the gap between the central feeding-venting tube and the external shaft is filled with a gas having a condensation temperature that is somewhat higher than the boiling temperature of the cryogenic liquid, wherein the solidification temperature of this gas is somewhat lower than the boiling temperature of the cryogenic liquid. This gas can be introduced into these gaps via the inlet-outlet connection installed on the proximal section of the external shaft.

A charging and purging technique can be used to realize the heat pipe principle described hereinabove. This technical solution allows heating the distal section of the external shaft at the expense of the heat provided to the intermediate and proximal sections of the external shaft from the surroundings.

It should be noted that the multi-way valve of the accessory system may be replaced by a set of shut-off valves installed on the communicating ducts, wherein the coordinated operation of this set of shut-off valves simulates the operation of the aforementioned multi-way valve.

The cryosurgical instrument of the present invention can be provided with a thermocouple positioned in the cryotip for measuring the temperature in the cryotip during of its use in a cryosurgical procedure.

In addition, if the cryosurgical instrument of the present invention is used in a cryocatheter implementation, this cryocatheter should be provided with a steering mechanism permitting bending of its distal section.

Furthermore, when the cryotip of the present invention is used in a cryocatheter (or cryoprobe) implementation, it may also be provided with an electrode for preliminary detection of electrical signal activity of different sites of the organ to be operated upon.

The cyclical operation of the cryosurgical instrument of the invention and its accessory system will be now described in detail.

In the first quarter time period, a portion of the cryogenic liquid is introduced via the feed pipe of the thermo-insulated tank into the duct (hereinafter also referred to as main duct) communicating between the multi-way valve and the inlet-outlet connection installed on the proximal end of the central feeding-venting tube. During this first quarter time period the state of the multi-way valve is in a position allowing flow of the cryogenic liquid from the feed pipe into the main duct Thereafter, in the second quarter time period, the state of the multi-way valve is changed in order to cease the flow of the cryogenic liquid from the thermo-insulated tank into the main duct and during the next quarter time period the multi-way valve is set into a position in which it communicates between the bottle comprising the pressurized gas and the main duct, thereby accelerating the velocity of the portion of the cryogenic liquid passing through the main duct and the central feeding-venting tube such that it rapidly reaches the porous coating of the cryotip.

In the third quarter time period, the supply of the pressurized gas is shut off by setting the state of the multi-way valve into a state which cuts off the connection between the proximal end of the main duct and the feed pipe. During this time period the cryogenic liquid is boiling in the porous coating of the cryotip which in effect causes elevation of the pressure of the cryogenic liquid vapor in the central feeding-venting tube and in the main duct.

In the fourth quarter time period, the multi-way valve is placed into a state that communicates between the main duct and the outlet communicating with the atmosphere or with the vacuum pump. The boiling of the cryogenic liquid in the porous coating of the cryotip may continue during this time period. The aforementioned quarter time periods may of course have different durations.

The cryosurgical instrument of the invention may be designed as a cryocatheter intended to treat a blood vessel in order to prevent restenosis. In such cases it may be advantageous to have the cryotip constructed from an elastic polymer. It is therefore important to keep relatively low excessive pressure in the internal chamber of the distal section of this cryocatheter with small deviation from its average value. These conditions are advantageously obtained by the cryocatheter of the invention that is constructed with the coaxial intermediate lumen as was previously described hereinabove. The outlet connection of the coaxial intermediate lumen is provided with a T-shaped manifold, which comprises a crossbar and a main section intersecting perpendicularly with the crossbar. A pressure gauge is installed on one end of the crossbar and an adjusting valve is installed on its other end, wherein this adjusting valve is communicated with the atmosphere or with the vacuum pump. Signals from the pressure gauge are sent to a pressure control unit, which provides corresponding control signals for the operation of the adjusting valve. It should be noted that the pressure control unit may be interconnected with the aforementioned control unit, and by doing so the operations of these control units can be correlated.

It is an object of the present invention to provide a flexible catheter with high flexibility, high specific freezing power and a sufficiently small diameter for cryosurgical procedures in different areas of medicine.

It is another object of the present invention to provide a rigid probe with high specific freezing power and a sufficiently small diameter for cryosurgical procedures in different areas of medicine.

It is an additional object of the invention to provide a cryosurgical instrument and a suitable accessory system having a high degree of safety and reliability, which are suitable for carrying out cryosurgical procedures. It is a further object of the present invention to provide a cryosurgical instrument capable of ensuring positive temperatures at the distal section of its external shaft, especially, in the vicinity of the cryotip.

It is yet another object of the present invention to provide a method for thermal insulation of the distal section of the external shaft a cryosurgical instrument that is based on a heat pipe principle.

It is still another object of the present invention to provide a cryocatheter that may be used for inhibiting restenosis of a blood vessel.

BRIEF DESCRIPTION OF THE SEVERAL VIEWS OF THE DRAWINGS

Other objectives of this invention will be apparent from the following detail description taken in conjunction with the accompanying drawings, in which.

DETAILED DESCRIPTION OF THE INVENTION

Figure 1:
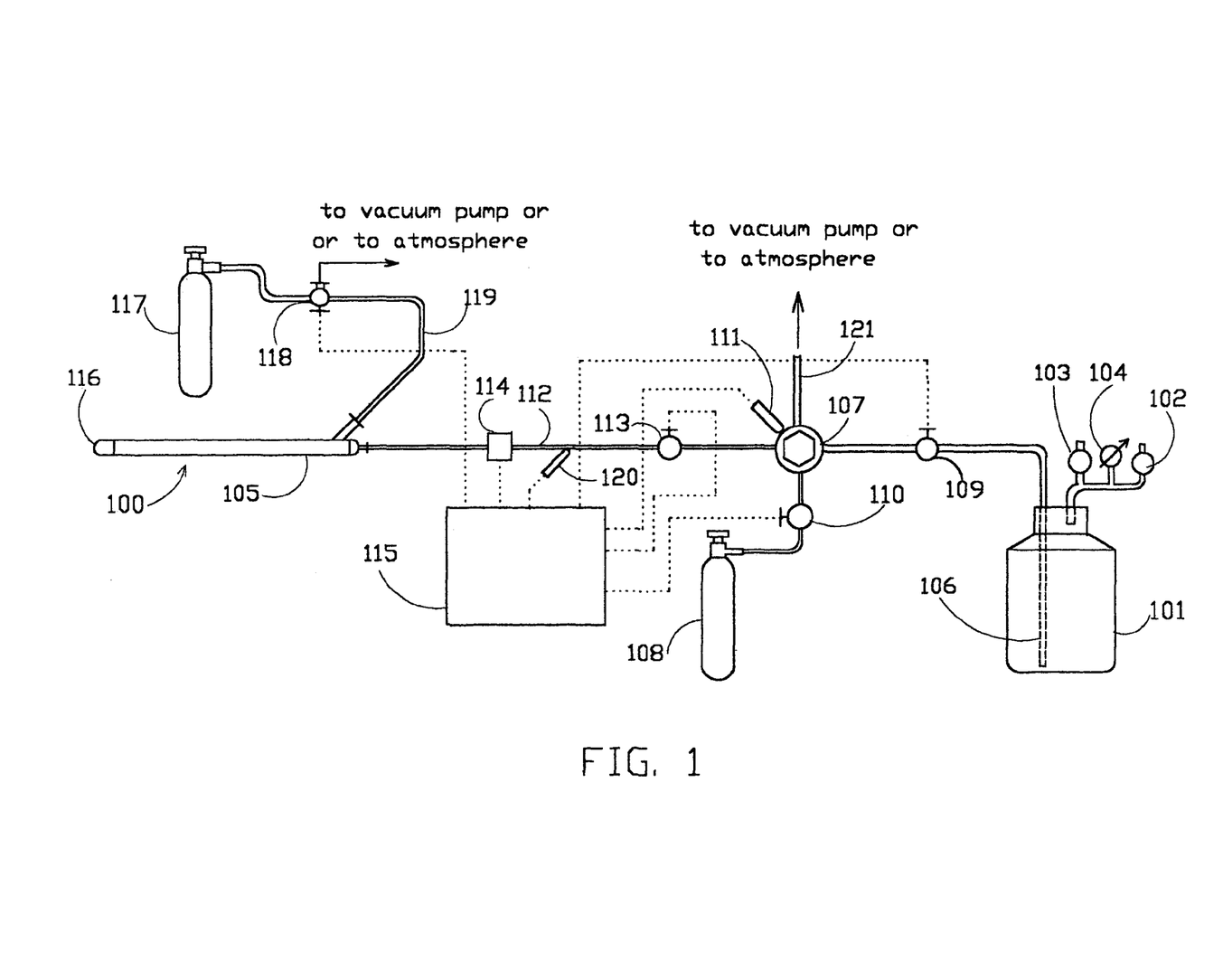
FIG. 1 shows a general view of a cryosurgical instrument and a block diagram of a respective accessory system according to one preferred embodiment of the invention.

FIG. 1 shows a general view of one preferred embodiment of the invention wherein the cryosurgical instrument comprises: a cryosurgical instrument 100 comprising cryotip 116 and an elongated tubular sub-unit 105; and wherein the accessory system comprises: a thermo-insulated tank (or a Dewar flask) 101 for supplying a cryogenic liquid contained therein, said thermo-insulated tank 101 is provided with a relief valve 103 that allows presetting a desired pressure in the thermo-insulated tank, a shut-off valve 102 is used for filling the thermo-insulated tank 101 with the cryogenic liquid, and manometer 104.

The multi-way valve 107 communicates between: a feeding pipe 106 situated in the thermo-insulated tank 101; a vacuum pump (or the atmosphere) via duct 121; the cryosurgical instrument 100 via a main duct 112: a first bottle 108 comprising pressurized gas. Sensor 111 is used for controlling the preset changeover frequency of the multi-way valve 107. In addition, there are pressure and temperature gauges 114 and 120 installed on the main duct 112. Data obtained from these sensor and gauges is processed by a control unit 115. Whenever a significant deviations of the measured parameters (pressure and/or temperature) from the preset values, the control unit 115 cuts off the shut-off valves 109, 110 and 113.

The accessory system further comprises a second bottle 117 for providing a gas having a low thermal conductivity contained therein, for example R14. The second bottle 117 is communicated via duct 119 with the external chamber of the cryosurgical instrument 100 (the gaps shown in FIGS. 4 and 5 between the internal surface of the external shaft of the cryosurgical instrument 100, and the outer surface of the coaxial tubular piece and of the proximal section of the central feeding-venting tube). A three-way valve 118 installed on duct 119 and used for filling the external chamber by a charging and purging technique that is typically performed before operating the cryosurgical instrument 100 and carrying out any cryogenic treatment.

Figure 2:
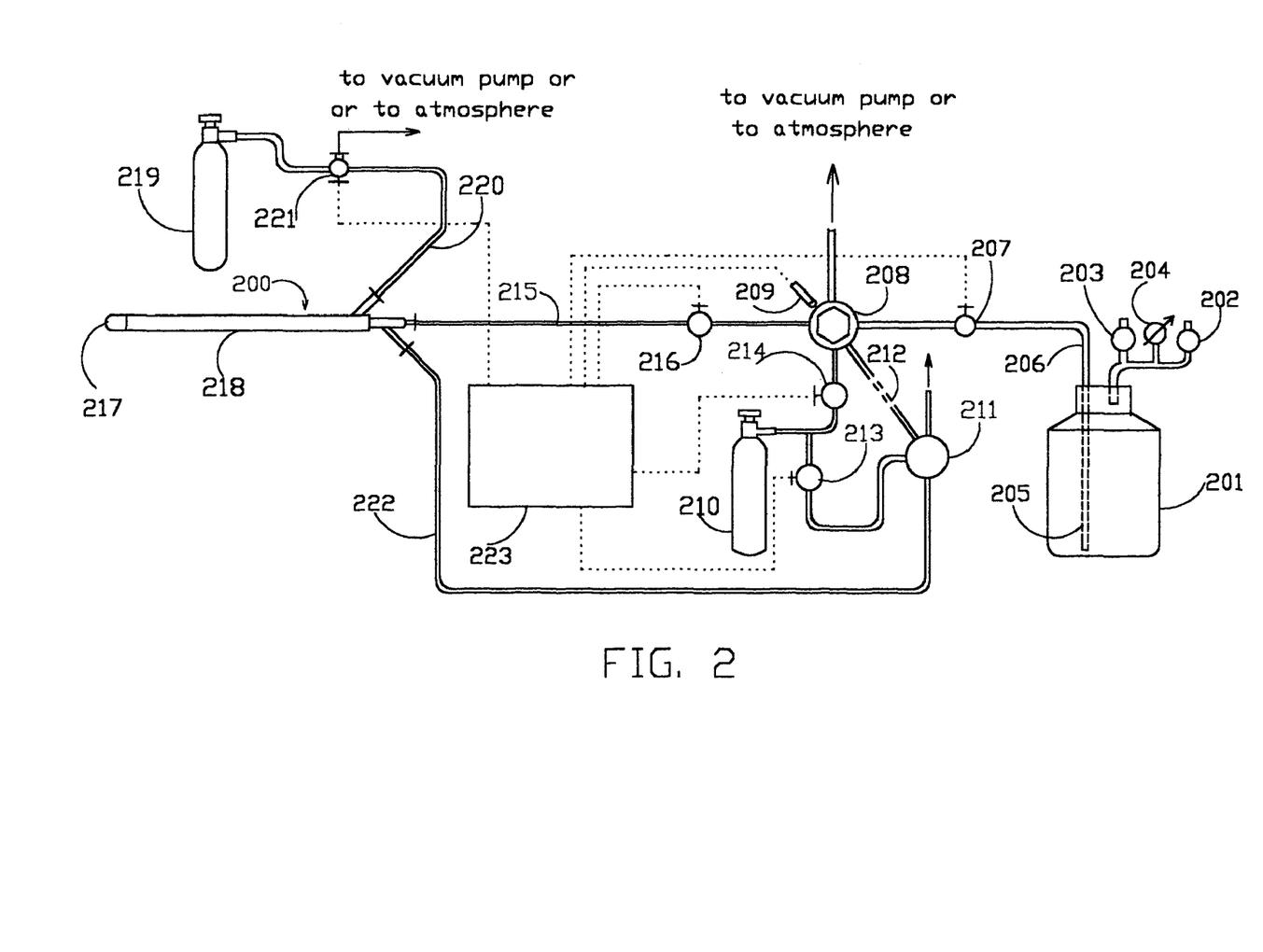
FIG. 2 shows a general view of a cryosurgical instrument and a block diagram of a respective accessory system according to another preferred embodiment of the invention.

FIG. 2 shows another preferred embodiment of the invention of a cryosurgical instrument 200 and its respective accessory system wherein there is an oscillating flow in the channel between the central feeding-venting lumen and the coaxial intermediate lumen of the cryosurgical instrument. Cryosurgical instrument 200 comprises two major sub-units: 1) cryotip 217; and 2) an elongated tubular sub-unit 218.

In this preferred embodiment the accessory system comprises a thermo-insulated tank (or a Dewar flask) 201 for supplying a cryogenic liquid contained therein. The thermo-insulated tank 201 is provided with a relief valve 203 which is used to preset a desired pressure in the thermo-insulated tank 201, with valve 202 which is used for filling the thermo-insulated tank 201 with the cryogenic liquid, and with manometer 204.

A multi-way valve 208 comprised in the accessory system communicates between: a feeding pipe 205 situated in the thermo-insulated tank 201; a vacuum pump or the atmosphere; the cryosurgical instrument 200 (via main duct 215); a first bottle 210 which supplies a pressurized gas contained therein.; the accessory system further comprise a three-way valve 211, which is coupled mechanically via coupling 212 to the multi-way valve 208. The three-way valve 211 is used to communicate the coaxial intermediate lumen (exemplified in FIGS. 4–7)—via duct 222, or the central feeding-venting tube of the cryosurgical instrument 200 via the multi-way valve 208, to the atmosphere (or vacuum pump) or to the first bottle 210 that is used for supplying a pressurized gas contained therein. A shut-off valve 213, is installed on the duct which communicates between the first bottle 210 and the three-way valve 211. Coupling 212 is designed to set the state of the three-way valve 211 into a state that communicates between duct 222 and the first bottle 210 whenever the multi-way valve 208 communicates between the main duct 215 and the atmosphere (or vacuum pump), and vice versa, namely—to set the state of the three-way valve 211 into a state that communicates between ducts 222 and the atmosphere (or vacuum pump) whenever the multi-way valve 208 communicates between the main duct 215 and the first bottle 210.

Sensor 209 is provided in the multi-way valve 208 and used for controlling its preset changeover frequency. Data obtained from this sensor is processed by a control unit 223. Whenever there are significant deviations of the measured parameters from the preset values, the control unit 223 closes the shut-off valve 207 that is installed on duct 206 and communicates between the feeding pipe 205 and the multi-way valve 208, a shut-off valve 214 installed on a duct communicating between the first bottle 210 and the multi-way valve 208, a shut-off valve 216 installed on the main duct 215, and a shut-off valve 213 installed on a duct communicating between first bottle 210 and the three-way valve 211.

The accessory system further comprise a second bottle 219 used for supplying a gas with low thermal conductivity contained therein, for example, R14. The second bottle 219 communicates via duct 220 with the external chamber (exemplified in FIGS. 4–7) of the cryosurgical instrument 200 (the gap between the external shaft of the cryosurgical instrument 200 and its coaxial intermediate lumen). A three-way valve 221 installed on duct 220 is used for filling the external chamber of the cryosurgical instrument 200 with a gas having low thermal conductivity by a charging and purging technique, which is typically performed before operating the cryosurgical instrument 200 and carrying out any cryogenic treatment.

Figure 3:
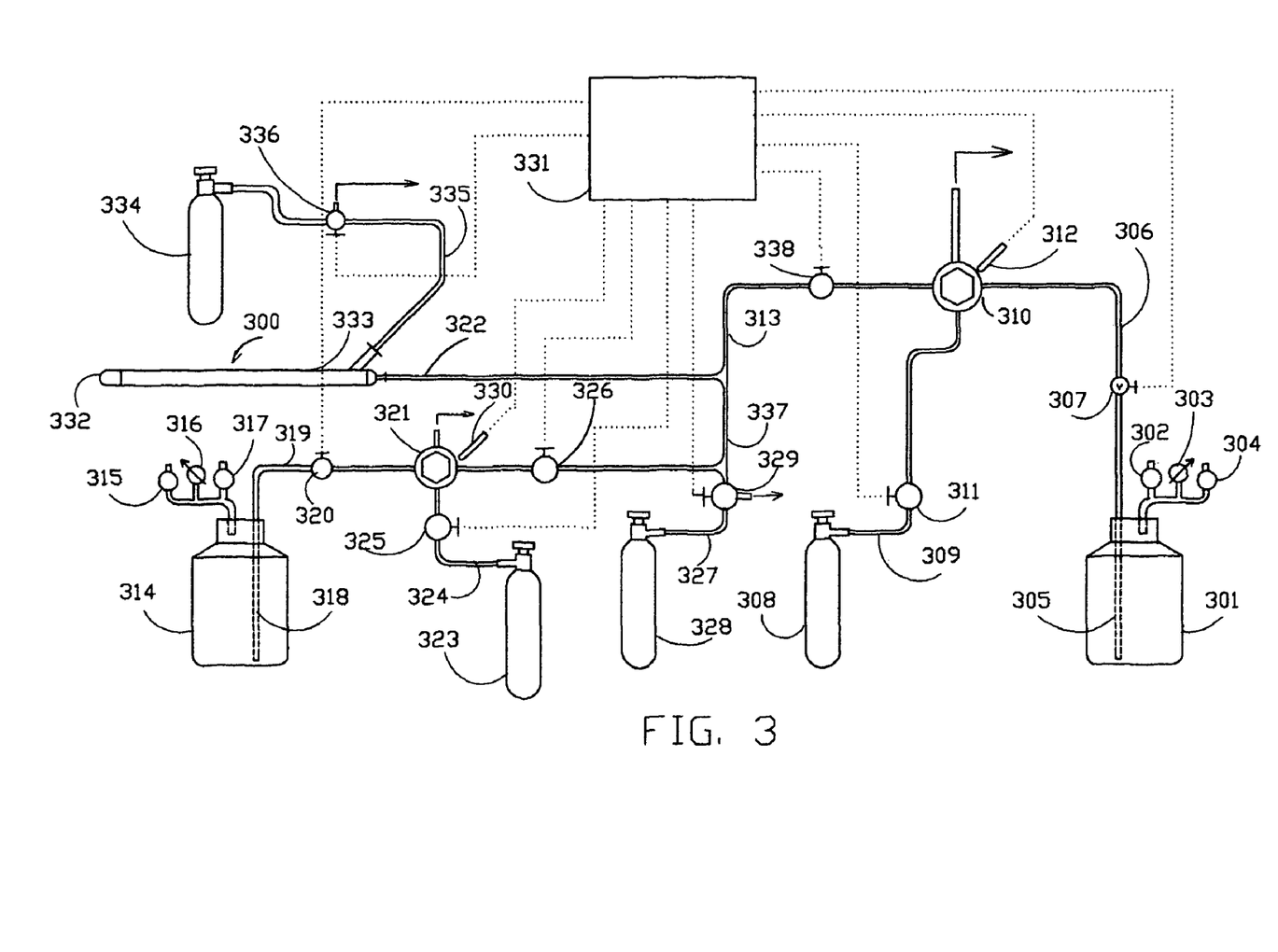
FIG. 3 shows a general view of a cryosurgical instrument and a block diagram of a respective accessory system according to a further preferred embodiment of the invention in which different liquids are used for preliminary ice-mapping and for carrying out a cryogenic treatment.

FIG. 3 shows a further preferred embodiment of the invention which comprises a cryosurgical instrument and a respective accessory system that is adapted to supply two different liquids which are used for carrying out preliminary ice-mapping and a cryogenic treatment.

FIG. 3 shows a cryosurgical instrument 300 with its cryotip 332 and an elongated tubular sub-unit 333, and a respective accessory system which comprises a first tank 301 used for supplying a first liquid contained therein which has cryogenic boiling temperature (for example, liquid nitrogen). The first tank 301 is provided with a relief valve 302 used for presetting the desired pressure in said first tank 301, valve 304 which is used for filling the first tank 301 with said first liquid, and with manometer 303.

The accessory system also comprise a multi-way valve 310 which communicates via duct 306 between: a feeding pipe 305 situated in the first tank 301; a vacuum pump or the atmosphere; the cryosurgical instrument 300 via a main duct 322, wherein the main duct splits into two ducts 313 and 337; and a first bottle 308 used for supplying a first pressurized gas contained therein. A shut-off valve 307 is installed on duct 306, a shut-off valve 338 is installed on duct 313, and a shut-off valve 309 is installed on a duct that communicates between the first bottle 308 and the multi-way valve 310. Sensor 312 is placed in the multi-way valve 310 for controlling its preset changeover frequency. Data obtained from this sensor is processed by a control unit 331, and whenever there are significant deviations of the measured parameter from a preset value, the control unit 331 closes the shut-off valves 307, 338 and 329.

The accessory system also comprises a second tank 314 used for supplying a second liquid contained therein and which has relatively high boiling temperature. The second tank 314 is provided with: a relief valve 315 that is used for presetting the desired pressure in the second tank 314; valve 317 used for filling the second tank 314 with the second liquid; and manometer 316.

A multi-way valve 321 is used for communicating between: a feeding pipe 318 that is situated in the second tank 314 (via duct 319) the atmosphere; the cryosurgical instrument 300 via the main duct 322 and duct 337; and a second bottle 323 with a second pressurized gas. A shut-off valve 320 is installed on duct 321, shut-off valve 325 is installed on duct 324 for communicating between the second bottle 323 and the multi-way valve 321, and a shut-off valve 326 is installed on duct 337. Sensor 330 is provided in the multi-way valve 321 and used for controlling its preset changeover frequency. Data obtained from sensor 330 is processed by the control unit 331, and whenever there are significant deviations of the measured parameter from a preset value, the control unit 331 closes the shut-off valves 320, 325 and 326.

A third bottle 328 is provided for supplying a third pressurized gas contained therein and which is communicated to the cryosurgical instrument 300 via ducts 327, 337 and 322. A three-way valve 329 is installed on duct 327 for communicating it with the atmosphere, according to control signal received from the control unit 331 which controls its state of operation. The three-way valve 329 is used for blowing out the ducts and the cryosurgical instrument 300 after carrying out an ice-mapping process in order to remove the second liquid and its vapors. Charging and purging technique is used to carry out the blowing out process.

A fourth bottle 334 is provided for supplying a gas with low thermal conductivity contained therein, for example, R14. The fourth bottle 334 is communicated via duct 335 with the external chamber (illustrated in FIGS. 4–7) of the cryosurgical instrument 300 (the gap between the external shaft of the cryosurgical instrument 300, and its coaxial tubular piece and the proximal section of the central feeding-venting tube). A three-way valve 336 installed on duct 335 is used for communicating it with the atmosphere and for filling the external chamber of the cryosurgical instrument 300 by charging and purging technique, which is typically performed previously to operating the cryosurgical instrument 300 and carrying out any cryogenic treatment.

Figure 4:
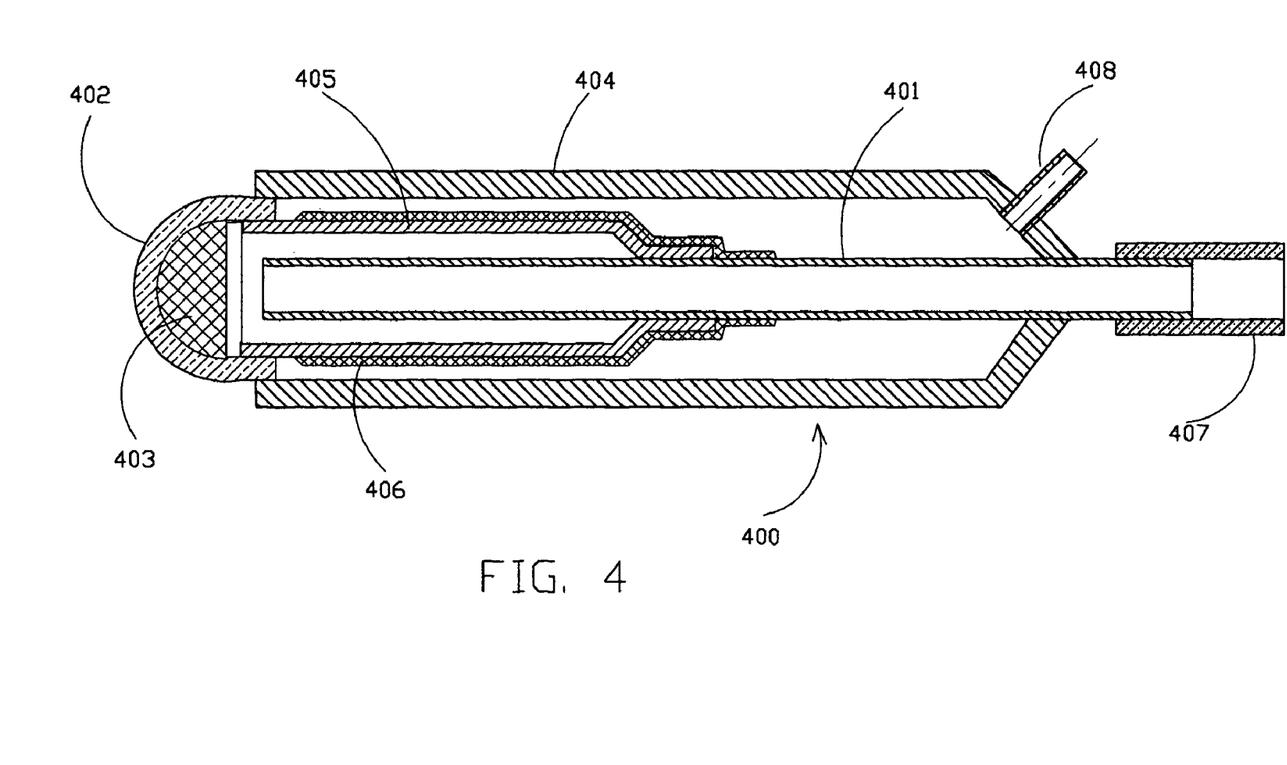
FIG. 4 shows an axial cross-section view of the cryosurgical instrument of the invention that is implemented with an active thermal insulation based on the heat pipe principle.

FIG. 4 shows an axial cross-section of a cryosurgical instrument 400 comprising an active thermal insulation based on a heat pipe principle.

A cryosurgical instrument 400 is constructed from two major sub-units: a distal cryotip 402 adapted for immediate contact with a target tissue, wherein the freezing action performed by this cryotip is obtained by evaporation of cryogenic liquid on its internal porous coating 403 which is formed from a porous metal with open porosity; and an elongated tubular sub-unit used for delivering portions of the cryogenic liquid on the internal porous coating 403 and for the removal of vapors generated in the boiling process of the cryogenic liquid in the internal porous coating 403.

The elongated tubular sub-unit comprises: an external shaft 404; a central feeding-venting tube 401 which is used for supplying portions of the cryogenic liquid to the internal porous coating 403 of the distal cryotip 402 and also for removal of vapors, which are generated in the process of boiling of the cryogenic liquid in the internal coating 403, into the atmosphere.

The elongated tubular sub-unit further comprises a coaxial tubular piece 405 positioned in the gap between the distal sections of the central feeding-venting tube and the external shaft 404; the distal end of the coaxial tubular piece 405 is sealed by cryotip 402, and its proximal end is sealed by the central feeding-venting tube 401.

The outer surfaces of the coaxial tubular piece 405 and a section of the central feeding-venting tube 401 mating this coaxial tubular piece are covered with a porous coating 406 with open porosity that is functioning as a wick when the gap between the external shaft 404, the coaxial tubular piece 405 and the mating section of the central feeding-venting tube 401 is filled with vapors of a gas that its condensation temperature is higher than the boiling temperature of the applied cryogenic liquid.

The proximal end of the feeding-venting central tube is provided with an inlet-outlet connection 407, and the proximal section of the external shaft 404 is provided with an inlet-outlet connection 408.

Figure 5:
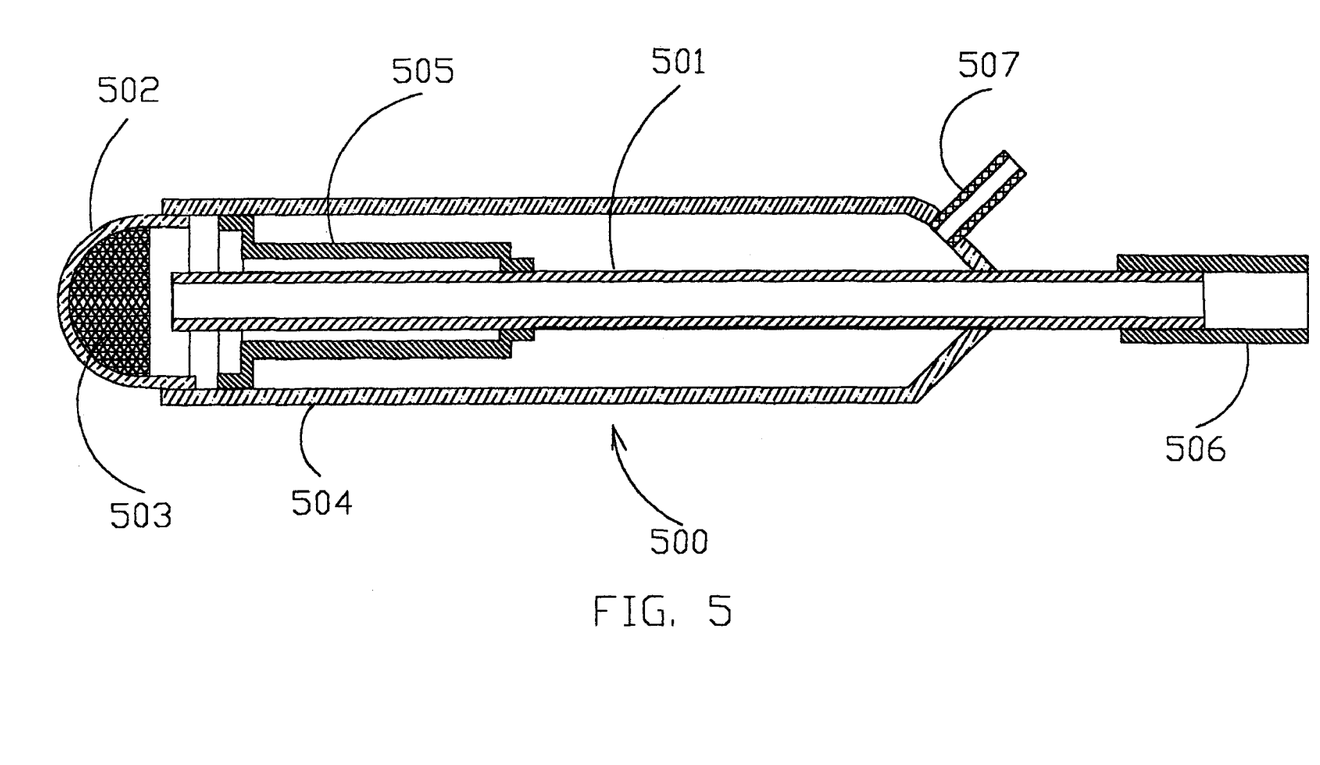
FIG. 5 shows an axial cross-section view of a cryosurgical instrument of the invention comprising a coaxial tubular piece joined at its distal end with the external shaft of the instrument.

FIG. 5 is an axial cross-section of a cryosurgical instrument 500 comprising a coaxial tubular piece 505 that is joined at its distal end with the external shaft 504 of the cryosurgical instrument 500.

Cryocatheter 500 (or cryoprobe) is constructed from two major sub units: a distal cryotip 502, which is used for contacting a target tissue, wherein the freezing action of cryotip 502 is obtained by evaporation of a cryogenic liquid in its internal porous coating 503, which is formed from porous metal with open porosity; an elongated tubular sub-unit used for delivering portions of the cryogenic liquid to the internal porous coating 503 and for removal of vapors generated in the process of the boiling the cryogenic liquid in the internal porous coating 503.

The elongated tubular sub-unit comprises an external shaft 504 and a central feeding-venting tube 501, which is used for supplying portions of the cryogenic liquid to the internal porous coating 503 of the distal cryotip 502 and for removal of vapors, generated in the process of boiling of the cryogenic liquid on the internal porous coating 503, into the atmosphere.

The elongated tubular sub-unit further comprises a coaxial tubular piece 505 positioned in the gap between the distal sections of the central feeding-venting tube 501 and the external shaft 504, wherein the distal end of the coaxial tubular piece 505 is sealed with the external shaft 504 and its proximal end is sealed by the central feeding-venting tube 501. The proximal end of the feeding-venting central tube 501 is provided with an inlet-outlet connection 506, and the proximal section of the external shaft 504 is provided with an inlet-outlet connection 507.

Figure 6:
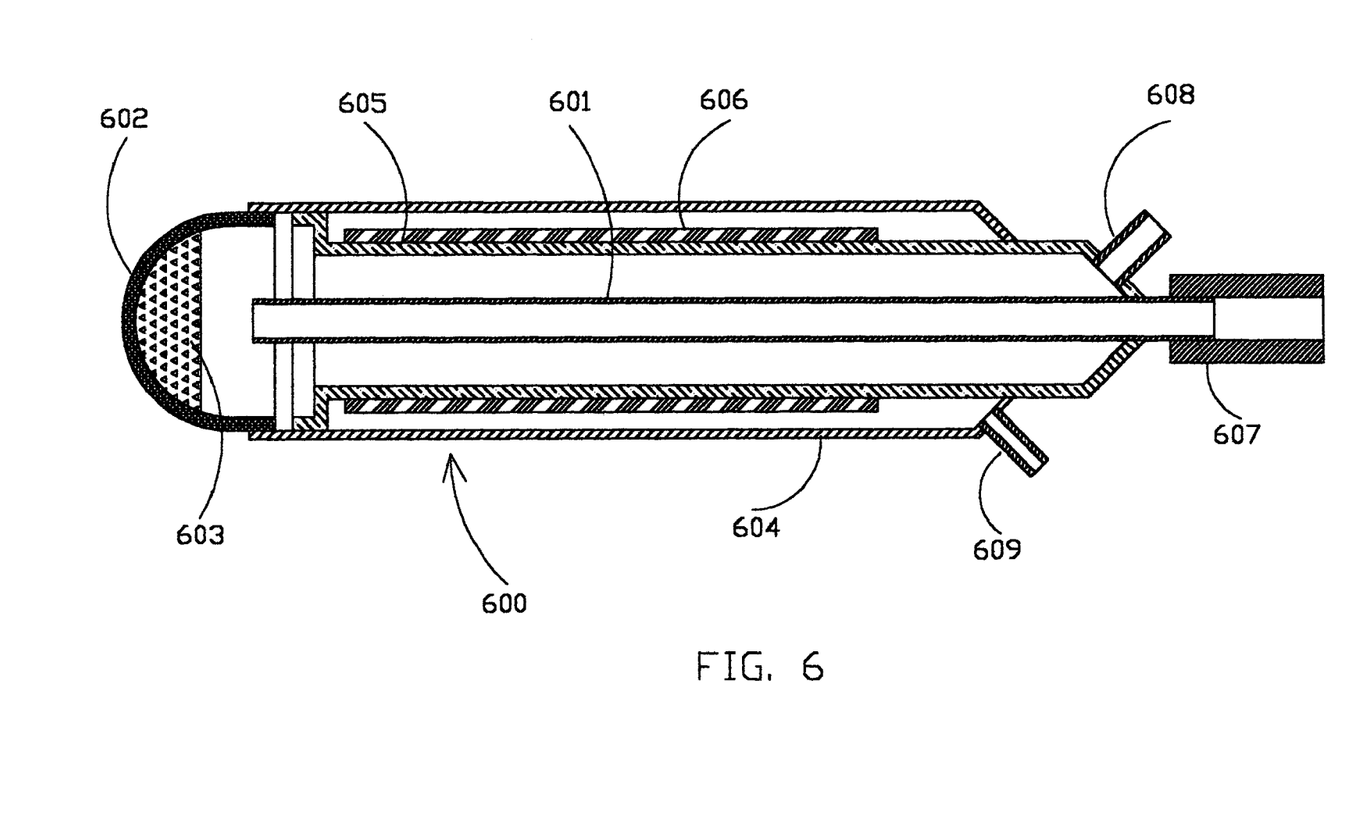
FIG. 6 shows an axial cross-section view of a cryosurgical instrument of the invention implemented with a coaxial intermediate lumen instead of the coaxial tubular piece.

FIG. 6 shows an axial cross-section of a cryosurgical instrument 600 comprising a coaxial intermediate lumen instead of the coaxial tubular piece that was used in the previously described cryosurgical instrument.

A cryosurgical instrument 600 is constructed from two major sub-units: a distal cryotip 602, which is used for contacting a target tissue, wherein the freezing action of cryotip 602 is obtained by evaporation of a cryogenic liquid on its internal porous coating 603 formed from porous metal with open porosity; and an elongated tubular sub-unit used for delivering portions of the cryogenic liquid to the porous coating and for removal of vapors generated in the boiling process of the cryogenic liquid in the internal porous coating 603.

The elongated tubular sub-unit comprises an external shaft 604 and a central feeding-venting tube 601, which is used for supplying portions of cryogenic liquid to the internal porous coating 603 of the distal cryotip 602 and for removal of the vapors, generated in the boiling process of the cryogenic liquid in the internal coating 603, into the atmosphere.

The elongated tubular sub-unit further comprises a coaxial intermediate lumen 605 positioned in the gap between the central feeding-venting tube 601 and the external shaft 604; the distal end of the coaxial intermediate lumen 605 is sealed by the external shaft 604 and its proximal end is sealed by the central feeding-venting tube 601. In addition, the proximal end of the external shaft 604 is sealed by the proximal section of the coaxial intermediate lumen 605. The proximal end of the feeding-venting central tube 601 is provided with an inlet-outlet connection 607, the proximal section of the external shaft 604 is provided with an inlet-outlet connection 609, and the proximal section of the coaxial intermediate lumen 605 is provided with an inlet-outlet connection 608. The outer surface of the coaxial intermediate lumen 605 is covered with a porous coating 606 starting at its distal end and ending near its proximal end. The porous coating 606 is used as a wick when a heat pipe principle is used for heating the distal section of the external shaft.

Figure 7:
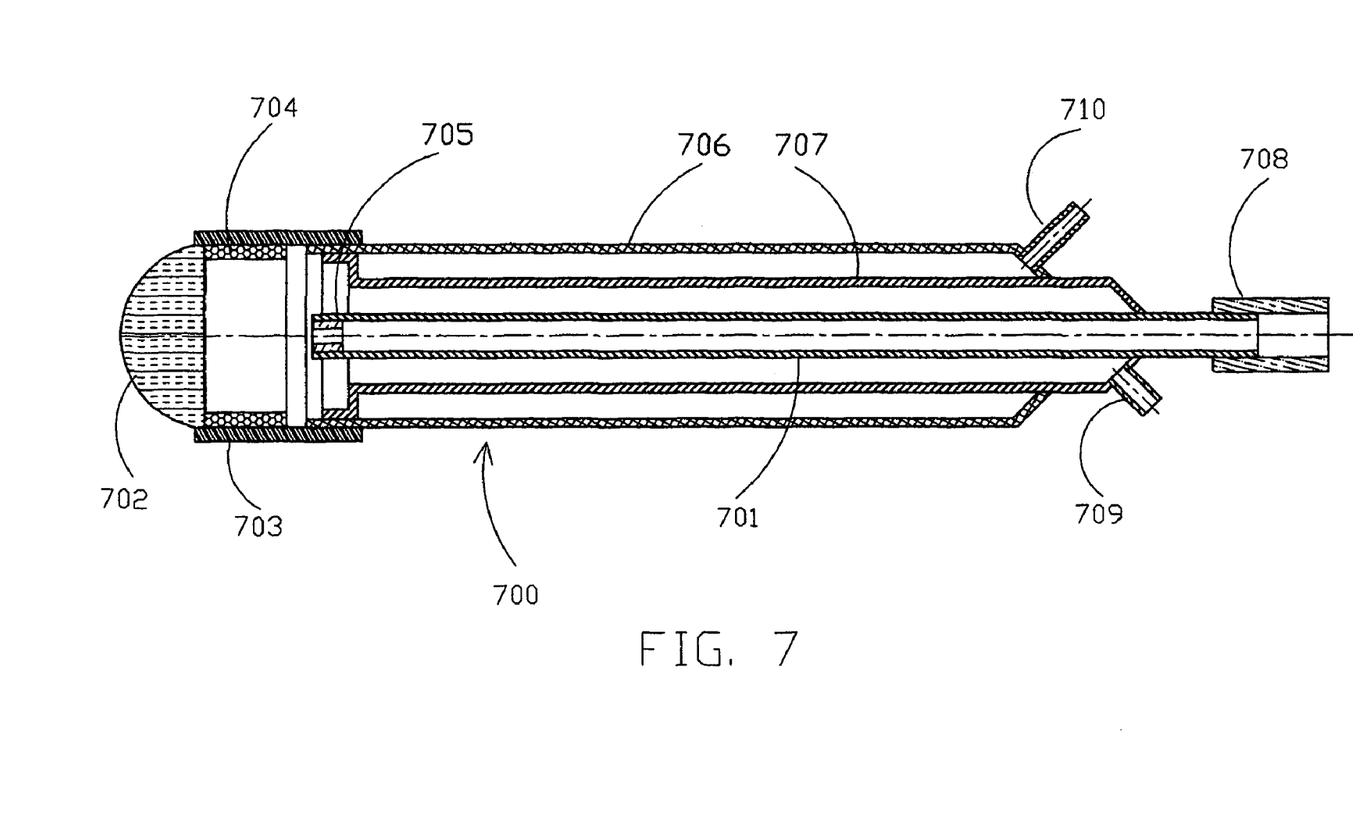
FIG. 7 shows an axial cross-section view of a cryocatheter of the invention that is suitable for preventing restenosis of blood vessels.

FIG. 7 shows an axial cross-section of a cryocatheter 700 adapted for preventing restenosis of blood vessels.

Cryocatheter 700 is constructed from two major sub-units: a distal cryotip, which is used for contacting a target tissue, wherein the freezing action of the cryotip is obtained by evaporation of a cryogenic liquid in an internal porous coating 704 formed from porous elastic polymer with open porosity which is provided on the internal surface of an external tubular piece 703 made from an elastic polymer.

The distal end of the external tubular piece 703 is sealed by plug 702 manufactured from a polymer material having low thermal conductivity.

An elongated tubular sub-unit is used for delivering portions of the cryogenic liquid to the internal porous coating 704 and for removal of vapors generated in the boiling process of the cryogenic liquid in the internal porous coating 704.

The elongated tubular sub-unit comprises an external shaft 706, and a central feeding-venting tube 701, which is used for supplying portions of the cryogenic liquid to the internal porous coating 704 and for removal of the vapors, generated in the boiling process of the cryogenic liquid in the internal porous coating 704, into the atmosphere.

Orifice 705 provided at the distal end of the central feeding-venting tube 701 is used for reducing the pressure in the internal chamber of the cryotip formed by plug 702 and in the external tubular piece 703 with the internal porous coating 704.

In addition, there is a coaxial intermediate lumen 707 positioned in the gap between the central feeding-venting tube 701 and the external shaft 706, wherein the distal end of this intermediate lumen 707 is sealed by the external shaft 706 and its proximal end is sealed by the central feeding-venting tube 701. The proximal end of the external shaft 706 is sealed by the proximal section of the coaxial intermediate lumen 707. The proximal end of the feeding-venting central tube 701 is provided with an inlet-outlet connection 708, the proximal section of the external shaft 706 is provided with an inlet-outlet connection 710, and the proximal section of the coaxial intermediate lumen 707 is provided with an inlet-outlet connection 709.

What is claim:

1. A cryosurgical instrument and an accessory system, suitable for operating said cryosurgical instrument, said cryosurgical instrument comprising: a distal cryotip, made from material with high thermal conductivity the internal surface of which is covered with a metal porous coating having open porosity; an elongated tubular sub-unit comprising an external shaft made from flexible or rigid material the distal end of which is sealed by a surface of said cryotip; a central feeding-venting tube situated therein and adapted for delivering a cryogenic liquid therethrough to an internal surface of said distal cryotip and for removing vapors generated in the process of boiling of said cryogenic liquid on the internal surface of said distal cryotip; a coaxial tubular piece positioned in the gap between the distal sections of said central feeding-venting tube and said external shaft; and an inlet-outlet connection provided at the proximal end of said central feeding-venting tube; wherein the distal end of said coaxial tubular piece is sealed by said external shaft or by said cryotip, and the proximal end of said coaxial tubular piece is sealed by said central feeding-venting tube, said accessory system comprises:
a thermo-insulated tank for supplying said cryogenic liquid; a feed pipe, the lower end of which is positioned near the bottom of said thermo-insulated tank; a multi-way valve comprising: a first inlet connected to an outlet connection of said feed pipe via a first duct, a second inlet connection communicated by a second duct with a bottle used to provide a pressurized gas, an outlet connection communicated via a third duct with the atmosphere or with a vacuum pump, and an inlet-outlet connection communicated with said inlet-outlet connection of said central feeding-venting tube of said cryosurgical instrument via a main duct;
an electromechanical or pneumatic drive for sequentially changing communication state between said inlet-outlet connection and said first, second and third ducts; a sensor used for controlling a changeover frequency of said multi-way valve; a set of four shut-off valves installed on said main, first, second and third ducts; and a control unit, for controlling said changeover frequency and said shut-off valves.

2. The cryosurgical instrument and accessory system of claim 1, wherein the cryotip is provided with a sensor for measuring the temperature of said cryotip.

3. The cryosurgical instrument and accessory system of claim 1, wherein the cryosurgical instrument is designed as a rigid cryoprobe.

4. The cryosurgical instrument and accessory system of claim 1, wherein the cryosurgical instrument is designed as a flexible cryocatheter.

5. The cryosurgical instrument and accessory system of claim 4, wherein the flexible cryocatheter is provided with a steering mechanism.

6. The cryosurgical instrument and accessory system of claim 4, wherein the flexible cryocatheter is provided with an electrode for detection of electrical signal activity of an organ to be treated.

7. A cryosurgical instrument and accessory system as claimed in claim 1, further comprising: an additional bottle for supplying a gas which has very low thermal conductivity via an inlet-outlet connection provided at a proximal section of the external shaft, a duct communicating between said additional bottle and said inlet-outlet connection of said external shaft, and a three-way valve for connecting said inlet-outlet connection to the atmosphere or to a vacuum pump, or to an outlet of said additional bottle.

8. A cryosurgical instrument and accessory system as claimed in claim 7, wherein the outer surfaces of the coaxial tubular piece and of a section of said central feeding-venting tube near said coaxial tubular piece are covered with a porous coating with open porosity, wherein said porous coating is functioning as a wick, and wherein the gap between said external shaft and said coaxial tubular piece, and its extension to the gap between said central feeding-venting tube and said external shaft, are filled with a gas supplied by the additional bottle, and wherein the condensation temperature of said gas is higher than the boiling temperature of the cryogenic liquid and its solidification temperature is lower than the boiling temperature of said cryogenic liquid.

9. The cryosurgical instrument and accessory system of claim 1, wherein a coaxial intermediate lumen is applied instead of the tubular piece, wherein said coaxial intermediate lumen is the lumen between the external shaft and the central feeding-venting tube, and wherein the distal end of said coaxial intermediate lumen is sealed by said external shaft and its proximal end is sealed by the proximal section of said central feeding-venting tube, and wherein the proximal end of said external shaft is sealed by the proximal section of said coaxial intermediate lumen, and wherein the proximal section of said coaxial intermediate lumen is provided with an outlet connection connected to an auxiliary shut-off valve installed on a duct communicating said outlet connection with the atmosphere or with a vacuum pump, and wherein said auxiliary shut-off valve is coupled to the multi-way valve mechanically or electro-mechanically such that it is opened during the time period in which said multi-way valve communicates the main duct with the first duct.

10. The cryosurgical instrument and accessory system of claim 9, wherein the outlet connection of the coaxial intermediate lumen is used as an auxiliary inlet-outlet connection for periodically receiving a gas supplied from an auxiliary bottle into the gap between said intermediate lumen and the central feeding-venting tube, wherein said gas is provided when the multi-way valve communicates said central feeding-venting tube and the atmosphere or a vacuum pump, and wherein a three-way valve is used instead of the auxiliary shut-off valve, and wherein said three-way valve is coupled mechanically by a coupling with said multi-way valve and provides connection to a channel between said coaxial intermediate lumen and said central feeding-venting tube, to the atmosphere or to a vacuum pump, or to a bottle used for supplying a pressurized gas, wherein a shut-off valve is installed on a duct communicating between said auxiliary bottle and said three-way valve, and wherein said coupling is designed such that when said multi-way valve communicates between the main duct and the atmosphere or said vacuum pump said three-way valve communicates between said auxiliary inlet-outlet connection and said auxiliary bottle, and vice versa, when said multi-way valve communicates between said main duct with said auxiliary bottle said three-way valve communicates between said auxiliary inlet-outlet connection and the atmosphere or said vacuum pump.

11. The cryosurgical instrument and accessory system as claimed in claim 4, wherein the cryosurgical instrument is designed as a flexible cryocatheter which is intended to treat a blood vessel in order to prevent restenosis, and wherein the cryotip of said cryosurgical instrument has a tubular shape the distal end of which is sealed by a plug made from polymer having a low thermal conductivity and its tubular section is fabricated from a thin polymer film with high elasticity, and wherein the internal surface of said cryotip is covered with a porous polymer layer with open porosity and which is of high elasticity.

12. The cryosurgical instrument and accessory system of claim 11, wherein the distal end of the central feeding-venting tube is provided with an orifice.

13. The cryosurgical and accessory system of claim 11, wherein the outlet connection of the intermediate lumen is provided with a T-shaped manifold, which comprises a crossbar and a main section intersecting perpendicularly with said crossbar, wherein a pressure gauge is installed on one end of said crossbar and an adjusting valve connected with the atmosphere or with a vacuum pump is installed on its other end, and wherein signals received from said pressure gauge are retrieved by a pressure control unit and used for determining the operation state of said adjusting valve.

14. The cryosurgical instrument and accessory system of claim 9, wherein at least the outer surface of the distal section of the coaxial intermediate lumen is covered by a coating with open porosity which operates as a wick, wherein the gap between the external shaft and said coaxial intermediate lumen is filled with a gas having a condensation temperature higher than the boiling temperature of the cryogenic liquid and having a solidification temperature which is lower than the boiling temperature of said cryogenic liquid, and wherein said gas is provided into said gap via the inlet-outlet connection installed in the proximal section of said external shaft.

15. The cryosurgical instrument and accessory system of claim 1, wherein said accessory system comprises two accessory sub-systems, each of which is similar in structure to the accessory system of claim 1, wherein said accessory sub-systems have a common control unit and a common main duct which splits off into two ducts communicated correspondingly with first and a second multi-way valves, and wherein a thermo-insulated tank of a first accessory sub-system is used to supply a cryogenic liquid for freezing a target tissue, and wherein a thermo-insulated tank of said second accessory sub-system is used for supplying a liquid with relatively high boiling temperature, and wherein said accessory system comprises an auxiliary accessory sub-system which serves for blowing out said cryosurgical instrument and the ducts communicating said first and second accessory sub-systems with said cryosurgical instrument, and wherein said auxiliary accessory sub-system comprise an auxiliary bottle used for supplying a pressurized gas and an auxiliary three-way valve installed on a duct communicating said auxiliary bottle with said main duct, and wherein said three-way valve is regulated by said control unit, and wherein said auxiliary three-way valve has two outlet connections the first of which is communicated with said main duct and the second of which is communicated with the atmosphere or with a vacuum pump.

16. The cryosurgical instrument and accessory system of claim 15, wherein the first, second and auxiliary accessory sub-systems comprise a common bottle used for supplying a pressurized gas.

17. The cryosurgical instrument and accessory system of claim 1, further comprising a pressure and/or temperature gauges installed on the main duct, wherein said temperature and pressure gauges provide data to said control unit.

18. The cryosurgical instrument and accessory system of claim 3, wherein the cryosurgical instrument is designed as a rigid cryoprobe, and wherein the external shaft is made from metal and its proximal section is not provided with the inlet-outlet connection, and wherein a gas having low thermal conductivity constantly fills the gap between said external shaft and the coaxial intermediate lumen, and wherein said accessory system does not comprise an auxiliary sub-system for filling said gap with said gas.

19. The cryosurgical instrument and accessory system as claimed in claim 10, wherein the cryosurgical instrument is designed as a flexible cryocatheter which is intended to treat a blood vessel in order to prevent restenosis, and wherein the cryotip of said cryosurgical instrument has a tubular shape the distal end of which is sealed by a plug made from polymer having a low thermal conductivity and its tubular section is fabricated from a thin polymer film with high elasticity, and wherein the internal surface of said cryotip is covered with a porous polymer layer with open porosity and which is of high elasticity.

20. The cryosurgical instrument and accessory system of claim 19, wherein the distal end of the central feeding-venting tube is provided with an orifice.

21. The cryosurgical and accessory system of claim 19, wherein the outlet connection of the intermediate lumen is provided with a T-shaped manifold, which comprises a crossbar and a main section intersecting perpendicularly with said crossbar, wherein a pressure gauge is installed on one end of said crossbar and an adjusting valve connected with the atmosphere or with a vacuum pump is installed on its other end, and wherein signals received from said pressure gauge are retrieved by a pressure control unit and used for determining the operation state of said adjusting valve.

22. The cryosurgical instrument and accessory system of claim 14, wherein the cryosurgical instrument is designed as a rigid cryoprobe, and wherein the external shaft is made from metal and its proximal section is not provided with the inlet-outlet connection, and wherein a gas having low thermal conductivity constantly fills the gap between said external shaft and the coaxial intermediate lumen, and wherein said accessory system does not comprise an auxiliary sub-system for filling said gap with said gas.

* * * * *